(12) United States Patent (10) Patent No.: US 10,206,568 B2
MacDougall (45) Date of Patent: Feb. 19, 2019

(54) HEAD MOUNTABLE DEVICE FOR MEASURING EYE MOVEMENT

(71) Applicant: Natus Medical Incorporated, San Carlos, CA (US)

(72) Inventor: Hamish MacDougall, Taastrup (DK)

(73) Assignee: Natus Medical Incorporated, Pleasanton, CA (US)

( * ) Notice: Subject to any disclaimer, the term of this patent is extended or adjusted under 35 U.S.C. 154(b) by 0 days.

(21) Appl. No.: 14/288,209

(22) Filed: May 27, 2014

(65) Prior Publication Data

US 2015/0335239 A1 Nov. 26, 2015

(30) Foreign Application Priority Data

May 23, 2014 (DK) .................................. 2014 70301
May 23, 2014 (EP) ..................................... 14169653

(51) Int. Cl.
*A61B 3/113* (2006.01)
*A61B 3/14* (2006.01)
(Continued)

(52) U.S. Cl.
CPC .............. *A61B 3/113* (2013.01); *A61B 3/145* (2013.01); *G02B 27/017* (2013.01);
(Continued)

(58) Field of Classification Search
CPC . G06F 3/01; G06F 3/011; G06F 3/012; G06F 3/013; G02B 27/00; G02B 27/01; G02B 27/017; G02B 2027/0138
(Continued)

(56) References Cited

U.S. PATENT DOCUMENTS 7,553,021 B2 * 6/2009 Fergason ............... A61B 3/113
351/205
7,819,818 B2 * 10/2010 Ghajar ................... A61B 3/113
340/540
(Continued)

FOREIGN PATENT DOCUMENTS

CN 103748599 A 5/2012
WO WO 2005/077259 A1 8/2005
(Continued)

OTHER PUBLICATIONS

First Technical Examination dated Dec. 3, 2014, for corresponding Danish Patent Application No. PA 2014 70301, 8 pages.
(Continued)

*Primary Examiner* — Robert E. Tallman
(74) *Attorney, Agent, or Firm* — Temmerman Law Office; Mathew J. Temmerman

(57) ABSTRACT

A head mountable device for measuring eye movement includes: a camera system comprising a first camera, wherein the camera system is configured to obtain a first set of images of a first eye of a user with a first frame rate and a first resolution; a processing unit configured to process the obtained first set of images and provide a processing unit output based on the first set of images; and an interface connected to the processing unit, for providing a device output based on the processing unit output; wherein the first frame rate is sufficient to allow the processing unit to detect eye saccades of the first eye.

15 Claims, 7 Drawing Sheets

(51) Int. Cl.
*G02B 27/01* (2006.01)
*A61B 3/00* (2006.01)

(52) U.S. Cl.
CPC ...... *A61B 3/0025* (2013.01); *G02B 2027/014* (2013.01); *G02B 2027/0138* (2013.01); *G02B 2027/0187* (2013.01)

(58) Field of Classification Search
USPC .................................. 351/205–206, 209–210
See application file for complete search history.

(56) References Cited

U.S. PATENT DOCUMENTS

| | | |
|---|---|---|
| 2005/0099601 A1 | 5/2005 | MacDougall et al. |
| 2005/0110950 A1* | 5/2005 | Thorpe ................. A61B 3/113 351/209 |
| 2007/0161875 A1 | 7/2007 | Epley |
| 2008/0049186 A1 | 2/2008 | MacDougall et al. |
| 2010/0016754 A1 | 1/2010 | Whillock et al. |
| 2010/0056274 A1* | 3/2010 | Uusitalo .............. G02B 27/017 463/31 |
| 2012/0021806 A1 | 1/2012 | Maltz |
| 2012/0022395 A1 | 1/2012 | Kinkingnehun et al. |
| 2012/0081666 A1 | 4/2012 | Kiderman et al. |
| 2012/0293773 A1* | 11/2012 | Publicover ............. A61B 3/113 351/210 |
| 2013/0114850 A1 | 5/2013 | Publicover et al. |
| 2014/0327881 A1 | 11/2014 | Kiderman |
| 2015/0223683 A1* | 8/2015 | Davidovics ............ A61B 3/113 351/210 |
| 2017/0176749 A1* | 6/2017 | Ouderkirk .......... G02B 27/0172 |

FOREIGN PATENT DOCUMENTS

| | | |
|---|---|---|
| WO | WO 2010/042557 A2 | 4/2010 |
| WO | WO 2013/117727 A1 | 8/2013 |

OTHER PUBLICATIONS

Extended European Search Report dated Dec. 8, 2014, for related EP Patent Application No. 14169653.4, 10 pages.
Hamis Gavin MacDougall, et al., "The Video Head Impulse Test (vHIT) Detects Vertical Semicircular Canal Dysfunction", PLOS ONE, vol. 8, issue 4, Apr. 2013, 10 pages.
Paolo Colagiorgio, et al., "A New Tool for Investigating the Functional Testing of the VOR", Frontiers in Neurology, vol. 4, Oct. 25, 2013.
Second Technical Examination and Search Report dated Sep. 10, 2015, for corresponding Danish Patent Application No. PA 2014 70301, 3 pages.

* cited by examiner

HEAD MOUNTABLE DEVICE FOR MEASURING EYE MOVEMENT

RELATED APPLICATION DATA

This application claims priority to and the benefit of Danish Patent Application No. PA 2014 70301, filed on May 23, 2014, pending, and European Patent Application No. 14169653.4, filed on May 23, 2014, pending. The entire disclosures of both of the above applications are expressly incorporated by reference herein.

FIELD

The present disclosure relates to a device for measuring eye movement, in particular a head mountable device for measuring eye movement in relation to ophthalmologic, vestibular, and/or neurologic tests.

BACKGROUND

There is an ongoing investigation towards developing measurement techniques and equipment for measuring eye movement. Various ophthalmologic, vestibular and neurologic tests exists which involves observing eye movements. Tests may comprise a patient being asked to visually follow an object, or movement of the patients head either voluntarily or by the clinician forcing the movement. For example, the head impulse test has previously been performed using subjective assessment by the clinician.

Tests may comprise measuring fast eye movements, e.g. eye saccades, lasting approximately between 20-200 ms and involving angular speed up to 900 deg/s. Such fast movements may be visual to the clinician, but may be difficult to quantify consistently.

It is desirable to circumvent subjective measurements and provide a possible standardized test, which is independent of the clinician or other person performing the test. Furthermore, in some environments, such as in pre hospital settings, it may be problematic, if not impossible, to accurately perform the test when relying on subjective measurements.

Previously, it has been tried to perform the head impulse test objectively using scleral search coils. However, scleral search coils are uncomfortable, complex, bulky and expensive, and therefore alternative solutions are continuously sought.

SUMMARY

There is a need for a device which avoids the use of subjective measures in ophthalmologic, vestibular and neurologic tests, and hence is able to reliably measure eye movement when performing various tests. The present disclosure provides a device and a method which provides objective and reproducible measurement of eye movement.

Accordingly, a head mountable device for measuring eye movement is provided. The head mountable device comprises a frame, a camera system, a processing unit, and an interface. The camera system comprises a first camera, wherein the camera system is configured to obtain a first set of images of a first eye of a user with a first frame rate and a first resolution. The processing unit is configured to process the obtained first set of images and provides a processing unit output based on the first set of images. The interface is connected to the processing unit, for providing a device output based on the processing unit output. The first frame rate is selected such as to enable the processing unit to detect eye saccades of the first eye.

Also disclosed is a method for measuring eye movement of a user using a head mountable device comprising a frame, a camera system, a processing unit and an interface connected to the processing unit. The method comprises: obtaining a first set of images of a first eye of the user by the camera system with a first frame rate and a first resolution, wherein the first frame rate is selected such as to enable the processing unit to detect eye saccades of the first eye; processing the obtained first set of images by the processing unit to provide a processing unit output based on the first set of images; and providing a device output by the interface based on the processing unit output.

The head mountable device used in the method may be the head mountable device for measuring eye movement as also disclosed. The method may be implemented with the device for measuring eye movement. At least a part of the method may be incorporated in software adapted to run in a processing unit, such as the processing unit of the device for measuring eye movement.

It is an advantage of the present disclosure that it enables fast and objective examination of ophthalmologic, vestibular and neurologic parameters. Objective examinations as an alternative to conventional subjective assessments may provide more reliable and consistent examinations. Hence, incorrect or unnecessary treatment may be avoided, and improved possibility of detecting changes in a patient's condition is provided.

The head mountable device comprises a frame. The frame may be configured to be fixated to the head of the user, e.g. by adjustable and/or elastic straps. The frame may be in the form a goggle, a helmet, a cap, and/or another head mountable equipment. In an embodiment, the frame is embodied as a goggle. The frame may be configured to fasten the head mountable device to the head of the user such as to prevent motion of the head mountable device relative to the head of the user. The frame may comprise the camera system and/or the processing unit and/or the interface.

The method may further comprise mounting the head mountable device and/or the frame to the head of the user.

The head mountable device may be operable without attached wires. The head mountable device may comprise a power supply, such as a battery power supply. The frame may comprise the power supply.

In some tests, it may be beneficial to be able to obtain images of both eyes of a user. Hence, the camera system may be configured to obtain a second set of images of a second eye of the user with a second frame rate, wherein the second frame rate is selected such as to enable the processing unit to detect eye saccades of the second eye.

The first camera may be configured to obtain the first set of images and the second set of images. Alternatively and/or additionally, the camera system may comprise a second camera configured to obtain the second set of images.

Obtaining the first set of images and/or the second set of images preferably enable detection of eye saccades of the first eye and/or of the second eye. Eye saccades may be very fast, e.g. eye saccades may last for only 20 ms. Therefore, the first frame rate and/or the second frame rate may be sufficiently high to enable reliable detection of eye saccades. For examples, the first frame rate and/or the second frame rate may be higher than 125 frames per second (fps), such as higher than 150 fps, such as higher than 175 fps, such as higher than 200 fps, such as 250 fps. In other examples, the first frame rate and/or the second frame rate may be less than 125 fps, but is still sufficiently high to allow the processing unit to detect eye saccades of the first eye and/or of the second eye.

The head mountable device may comprise a first mirror for mirroring images of the first eye towards the first camera, and/or for mirroring images of the first eye towards the second camera, and/or for mirroring images of the second eye towards the first camera, and/or for mirroring images of the second eye towards the second camera. Additionally, the head mountable device may comprise a second mirror for mirroring images of the second eye towards the first camera and/or for mirroring images of the second eye towards the second camera.

The first camera and/or the second camera may be focused on the first and/or second eye. The first camera and/or the second camera may be focused on the first and/or second eye via the first and/or second mirror.

The head mountable device may comprise a first light source for emitting first electromagnetic radiation towards the first eye and/or the second eye. The first mirror and/or the second mirror may be configured to direct at least a part of the first electromagnetic radiation towards the first eye and/or the second eye.

The head mountable device may comprise a second light source for emitting second electromagnetic radiation towards the first and/or second eye. The first mirror and/or the second mirror may be configured to direct at least a part of the second electromagnetic radiation towards the first eye and/or the second eye.

The first and/or second electromagnetic radiation may comprise infrared radiation, laser radiation, visible red radiation, visible blue radiation, visible green radiation, and/or visible orange radiation. The first and/or second electromagnetic radiation may comprise electromagnetic radiation with wavelengths in the range of 380-450 nm, or in the range of 450-495 nm, or in the range of 495-570 nm, or in the range of 570-590 nm, or in the range of 590-620 nm, or in the range of 620-750 nm, or in the range of 750-2.500 nm, or in the range of 2.500-10.000 nm, or in the range of 10.000-1.000.000 nm.

The first and/or second light source may be used for testing the first and/or second eye's response to light. The first and/or second light source may be used to light up the first and/or second eye. The first and/or second light source may be used to light up the first and/or second eye for the camera system to obtain images of the first and/or second eye.

The camera system and/or the first camera and/or second camera may be configured to detect the first electromagnetic radiation and/or the second electromagnetic radiation.

The first and/or second mirror may be partly transparent. For example, the first and/or second mirror may be transparent to one or more selected ranges of electromagnetic radiation. The first and/or second mirror may be transparent to visible light, such as electromagnetic radiation with wavelengths in the range of 380-750 nm.

The frame may comprise the first and/or second mirror. The frame may comprise the first and/or second light source.

The head mountable device may comprise a first motion sensor configured to detect movement of the head mountable device. The frame may comprise the first motion sensor.

The first motion sensor may be configured to output a sensor output. The sensor output may be indicative of spacious orientation and/or movement of the head mountable device. The method may further comprise detecting movement of the head mountable device, e.g. by the first motion sensor. The processing unit may be connected to the first motion sensor, and the processing unit may be configured to process a sensor output from the first motion sensor. The processing unit output may be based on the sensor output. The processing unit output may be based on a comparison between the sensor output and the first and/or second set of images. The processing unit output may comprise one or more control signals and/or one or more data signals, such as data streams.

The first motion sensor may comprise one or more cameras. The first motion sensor may comprise one or more gyroscopes. The first motion sensor may comprise one or more accelerometers. The one or more cameras of the first motion sensor may be configured to detect movement relative to surroundings based on relative movements of objects in the field of view of the one or more cameras. The one or more gyroscopes of the first motion sensor may be configured to obtain angular velocity of the head mountable device, such as angular velocity of the head mountable device in three dimensions. The one or more accelerometers of the first motion sensor may be configured to obtain linear accelerations of the head mountable device, such as linear accelerations of the head mountable device in three dimensions.

The processing unit output may be indicative of one or more parameters of the user, such as an ophthalmologic parameter of the user, a vestibular parameter of the user, and/or a neurologic parameter of the user.

The processing unit may determine an ophthalmologic parameter of the user based on the first set of images and/or the second set of images. Determining of the ophthalmologic parameter may comprise performing an ophthalmologic examination, or a part of an ophthalmologic examination.

The method may further comprise moving the head of the user. Some tests may comprise detecting both movement of the head and movement of the first and/or second eye. Some tests may comprise detecting simultaneous movement of the head and movement of the first and/or second eye. Moving the head of the user may be induced by an operator while the user relaxes, and/or the moving of the head of the user may be induced voluntarily by the user.

The processing unit may determine a vestibular parameter of the user based on the first set of images and/or the second set of images and the sensor output. Determining of the vestibular parameter may comprise performing a vestibular examination, or a part of a vestibular examination.

The processing unit may determine a neurologic parameter of the user based on the first set of images and/or the second set of images and the sensor output. Determining of the neurologic parameter may comprise performing a neurologic examination, or a part of a neurologic examination.

The processing unit may receive the sensor output and the first and/or second set of images, and the vestibular parameter and/or the neurologic parameter of the user may be based on the sensor output and the first and/or second set of images.

The processing unit output may be indicative of a test result, such as an examination result. For example, the processing unit output may be indicative of a disorder of the user, such as an ophthalmologic disorder, a vestibular disorder, and/or a neurologic disorder. Alternatively or additionally, the processing unit output may comprise a plurality of output images based on the first set of images. For example, the plurality of output images may provide the operator, such as an examiner, the opportunity to verify the test result.

The device output may be indicative of one or more parameters of the user, such as an ophthalmologic parameter of the user, a vestibular parameter of the user, and/or a neurologic parameter of the user. The device output may be indicative of a test result, such as an examination result. For example, the device output may be indicative of a disorder of the user, such as an ophthalmologic disorder, a vestibular disorder, and/or a neurologic disorder. Alternatively and/or additionally, the device output may comprise a plurality of output images based on the first set of images. For example, the plurality of output images may provide the operator, such as an examiner, the opportunity to verify the test result.

The interface may comprise one or more types of interfaces for providing the device output to a user and/or an operator of the head mountable device.

The interface may comprise a docking interface for docking the head mountable device in a docking station. The interface may transfer the device output to a receiver in the docking station upon docking of the head mountable device. The docking interface may utilize a connection such as FireWire connection, USB connection, USB 2.0, USB 3.0, and/or near field communication.

The interface may comprise a display, such as a first display and/or a second display. The first display and/or the second display may be an organic light emitting diode (OLED), an OLED display, a light emitting diode (LED), an LED display, and/or an e-ink display. The first display and/or the second display may visually provide the device output, or part of the device output, to a user or an operator. The device output may comprise a visual output.

The interface may comprise a speaker, such as a first speaker and/or a second speaker. The first speaker and/or the second speaker may audiologically provide the device output, or part of the device output, to a user or an operator. The device output may comprise an audiologic output.

The interface may comprise a wireless transmitter unit. The interface may comprise a wireless transceiver unit comprising the wireless transmitter unit and a wireless receiver unit. The wireless transmitter unit and/or the wireless transceiver unit and/or the wireless receiver unit may operate according to Bluetooth, WiFi, 3G, and/or 4G.

Providing the device output may comprise transmitting the device output wirelessly to an external display. The wireless transmitter unit may be configured to transmit the device output, or a part of the device output, to a display, such as an external display. The external display may be external to the head mountable device. The external display may be external to the frame of the head mountable device. The external display may be a display of a smartphone, a tablet computer, a laptop, a TV, a smart-TV, and/or the like.

The first display, the second display, and/or the external display may be configured to provide a plurality of output images based on the first and/or second set of images to a user or an operator, thereby giving the user and/or the operator the opportunity to verify the test result or to observe the first and/or second eye of the user. The plurality of output images may provide a preview, such as a live preview, of the first and/or second set of images. The plurality of output images may be provided with a latency of less than 100 ms, such as less than 50 ms, such as less than 10 ms, from the obtaining of the first set of images. Thereby providing a live preview, or a near to live preview, of the first set of images. The wireless transmitter unit may be configured to transmit the device output, or part of the device output, as a live stream. For example, the wireless transmitter unit may be configured to transmit the device output, or part of the device output, to the external display with a latency of less than 100 ms, such as less than 50 ms, such as less than 10 ms, from the obtaining of the first set of images.

To facilitate live streaming of the device output, the device output may comprise reduced or compressed data. The processing unit may be configured to compress and/or reduce the amount of data in the processing unit output. The processing unit output may comprise a first secondary set of images with a first secondary frame rate and a first secondary resolution. The first secondary set of images may be visually corresponding to the first set of images. The processing unit output may comprise a second secondary set of images with a second secondary frame rate and a second secondary resolution. The second secondary set of images may be visually corresponding to the second set of images. The first secondary frame rate may be smaller than the first frame rate. Alternatively or additionally, the first secondary resolution may be smaller than the first resolution. The second secondary frame rate may be smaller than the second frame rate. Alternatively or additionally, the second secondary resolution may be smaller than the second resolution.

The processing unit may be configured to compress an initial processing unit output based on the first set of images. The size of the processing unit output may be below 20%, such as below 15%, such as below 5%, of the size of the initial processing unit output. Substantial compression or reduction of data may provide increased opportunities for streaming data, especially if streaming data via a wireless transmitter.

The interface may comprise an input device for enabling control of the head mountable device. The input device may be the wireless receiver. Alternatively or additionally, the input device may comprise a touch display, a push button and/or a switch.

It is envisaged that any embodiments or elements as described in connection with any one aspect may be used with any other aspects or embodiments, mutatis mutandis.

The present invention will now be described more fully hereinafter with reference to the accompanying drawings, in which exemplary embodiments of the invention are shown. The invention may, however, be embodied in different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout. Like elements will, thus, not be described in detail with respect to the description of each figure.

A head mountable device for measuring eye movement includes: a camera system comprising a first camera, wherein the camera system is configured to obtain a first set of images of a first eye of a user with a first frame rate and a first resolution; a processing unit configured to process the obtained first set of images and provide a processing unit output based on the first set of images; and an interface connected to the processing unit, for providing a device output based on the processing unit output; wherein the first frame rate is sufficient to allow the processing unit to detect eye saccades of the first eye.

Optionally, the first frame rate is higher than 125 frames per second.

Optionally, the head mountable device further includes a first mirror for mirroring images of the first eye towards the first camera.

Optionally, the head mountable device further includes a first light source for emitting first electromagnetic radiation towards the first eye.

Optionally, the first mirror is configured to direct at least a part of the first electromagnetic radiation towards the first eye.

Optionally, the camera system is configured to obtain a second set of images of a second eye of the user with a second frame rate, wherein the second frame rate is sufficient to allow the processing unit to detect eye saccades of the second eye.

Optionally, the second frame rate is higher than 125 frames per second.

Optionally, the camera system comprises a second camera configured to obtain the second set of images.

Optionally, the processing unit output is indicative of an ophthalmologic parameter of the user.

Optionally, the head mountable device further includes a frame, wherein the camera system, the processing unit, and the interface are mounted to the frame.

Optionally, the head mountable device further includes a first motion sensor configured to detect a movement of the head mountable device; wherein the processing unit is connected to the first motion sensor; wherein the processing unit is configured to process a sensor output from the first motion sensor; and wherein the processing unit output is also based on the sensor output.

Optionally, the first motion sensor comprises a camera, a gyroscope, an accelerometer, or any combination of the foregoing; and wherein the camera is the first camera or another camera.

Optionally, the processing unit output is indicative of a vestibular parameter of the user.

Optionally, the processing unit is configured to receive the sensor output and the first set of images, and wherein the vestibular parameter of the user is based on the sensor output and the first set of images.

Optionally, the processing unit output is indicative of a neurologic parameter of the user.

Optionally, the processing unit is configured to receive the sensor output and the first set of images, and wherein the neurologic parameter of the user is based on the sensor output and the first set of images.

Optionally, the head mountable device further includes a frame, wherein the first motion sensor is mounted to the frame.

Optionally, the interface comprises a wireless transmitter unit.

Optionally, the wireless transmitter unit is configured to transmit the device output to an external display, and wherein the external display is external to the head mountable device.

Optionally, the wireless transmitter unit is configured to transmit the device output to the external display with a latency of less than 10 ms from a time when the first set of images is obtained by the camera system.

Optionally, the processing unit output comprises a first secondary set of images with a first secondary frame rate and a first secondary resolution.

Optionally, the first secondary frame rate is smaller than the first frame rate, and/or the first secondary resolution is smaller than the first resolution.

Optionally, the processing unit is configured to compress an initial processing unit output based on the first set of images, wherein a size of the processing unit output is below 5% of a size of the initial processing unit output.

Optionally, the interface comprises a first display.

Optionally, the interface comprises a speaker.

Optionally, the interface comprises an input device for allowing control of the head mountable device.

Optionally, the processing unit output is indicative of a test result.

Optionally, the processing unit output comprises a plurality of output images based on the first set of images.

A method for measuring eye movement of a user using a head mountable device comprising a camera system, a processing unit, and an interface connected to the processing unit, the method includes: obtaining a first set of images of a first eye of the user by the camera system, the first set of images having a first frame rate and a first resolution, wherein the first frame rate is sufficient to allow the processing unit to detect eye saccades of the first eye; processing the obtained first set of images by the processing unit to provide a processing unit output based on the first set of images; and providing a device output by the interface based on the processing unit output.

Optionally, the first frame rate is higher than 125 frames per second.

Optionally, the method further includes mounting the head mountable device to a head of the user.

Optionally, the head mountable device comprises a first motion sensor, and wherein the method further comprises detecting a movement of the head mountable device by the first motion sensor.

Optionally, the device output is indicative of a vestibular parameter of the user.

Optionally, the device output is indicative of an ophthalmologic parameter of the user.

Optionally, the device output is indicative of a neurologic parameter of the user.

Optionally, the device output comprises an audiologic output.

Optionally, the device output comprises a visual output.

Optionally, the act of providing the device output comprises transmitting the device output wirelessly to an external display.

Optionally, the device output is indicative of a test result.

Other and further aspects and features will be evident from reading the following detailed description.

BRIEF DESCRIPTION OF THE DRAWINGS

The above and other features and advantages will become readily apparent to those skilled in the art by the following detailed description of exemplary embodiments thereof with reference to the attached drawings, in which.

DETAILED DESCRIPTION

Figure 1:
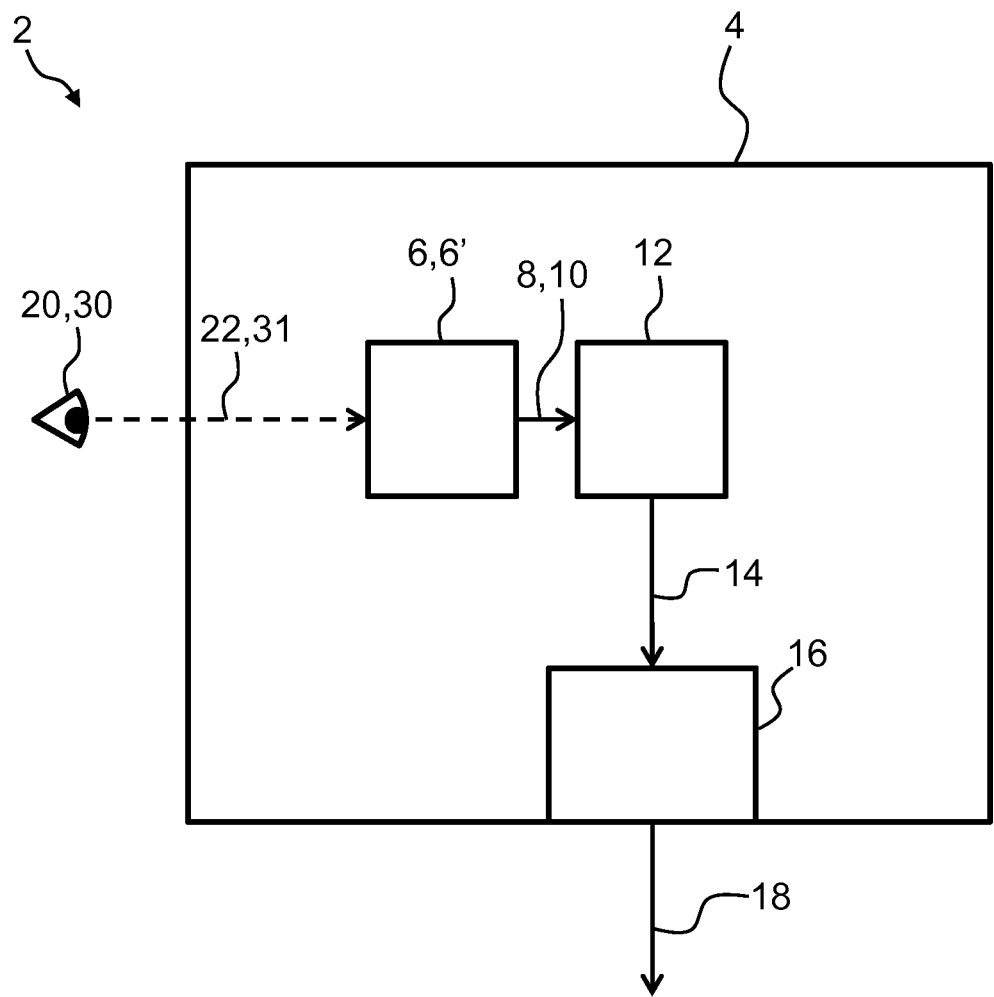
FIG. 1 schematically illustrates an exemplary head mountable device.

Various features are described hereinafter with reference to the figures. It should be noted that the figures may or may not be drawn to scale and that the elements of similar structures or functions are represented by like reference numerals throughout the figures. It should be noted that the figures are only intended to facilitate the description of the features. They are not intended as an exhaustive description of the claimed invention or as a limitation on the scope of the claimed invention. In addition, an illustrated feature needs not have all the aspects or advantages shown. An aspect or an advantage described in conjunction with a particular feature is not necessarily limited to that feature and can be practiced in any other features even if not so illustrated or if not so explicitly described.

FIG. 1 schematically illustrates an exemplary head mountable device 2. The head mountable device 2 comprises a frame 4, a camera system 6, 6', a processing unit 12, and an interface 16.

The camera system 6, 6' is configured to obtain a first set of images 8 of a first eye 20 of a user with a first frame rate and a first resolution. Alternatively or additionally, the camera system 6, 6' may be configured to obtain a second set of images 10 of a second eye 30 of the user with a second frame rate and a second resolution. The camera system 6, 6' obtains images 22 of the first eye 20 and converts the images 22 of the first eye 20 to the first set of images 8 of the first eye 20. Alternatively or additionally, the camera system 6, 6' obtains images 31 of the second eye 30 and converts the images 31 of the second eye 30 to the second set of images 10 of the second eye 30.

The first frame rate and/or the second frame rate is/are high enough to enable detection of eye saccades of the first eye 20 and/or the second eye 30, respectively. Eye saccades in humans may last less than 20 ms. High frame rate may enable enhanced detection of eye saccades. For example, the first frame rate and/or the second frame rate may be higher than 125 fps.

The processing unit 12 is configured to process the obtained first set of images 8 and/or the second set of images 10. The processing unit 12 provides a processing unit output 14 based on the first set of images 8. The processing unit output 14 may comprise data and/or one or more control signals.

The interface 16 is connected to the processing unit 12. The interface provides a device output 18, based on the processing unit output 14. The device output 18 may be an electronic signal and/or an optical signal and/or a visual signal and/or an audible signal. The device output 18 may comprise a control signal and/or a data signal.

The processing unit 12 may be configured to compress and/or reduce the amount of data in the processing unit output 14. For example, in order for the interface 16 to transmit the device output 18, or a part of the device output 18, wirelessly, without substantial delay e.g. a delay of the order of 10 ms, the processing unit output 14 may be compressed and/or reduced. For example, the processing unit output 14 may comprise a first secondary set of images with a first secondary frame rate and a first secondary resolution, wherein the first secondary frame rate is smaller than the first frame rate and/or the first secondary resolution is smaller than the first resolution. Alternatively and/or additionally the processing unit output 14 may comprise a second secondary set of images with a second secondary frame rate and a second secondary resolution, wherein the second secondary frame rate is smaller than the second frame rate and/or the second secondary resolution is smaller than the second resolution.

Additionally and/or alternatively, the processing unit 12 may be configured to compress an initial processing unit output based on the first set of images 8 and/or the second set of images 10, wherein the size of the processing unit output 14 is below 20%, such as 10%, such as 5% of the size of the initial processing unit output.

The processing unit output 14 may be indicative of an ophthalmologic parameter of the user. For example, the processing unit 12 may receive a set of images, e.g. the first set of images 8 and/or the second set of images 10. Hence, the ophthalmologic parameter of the user may be based on the set of images, e.g. the first set of images 8 and/or the second set of images 10. The device output 18 may consequently also be indicative of the ophthalmologic parameter of the user.

Figure 2:
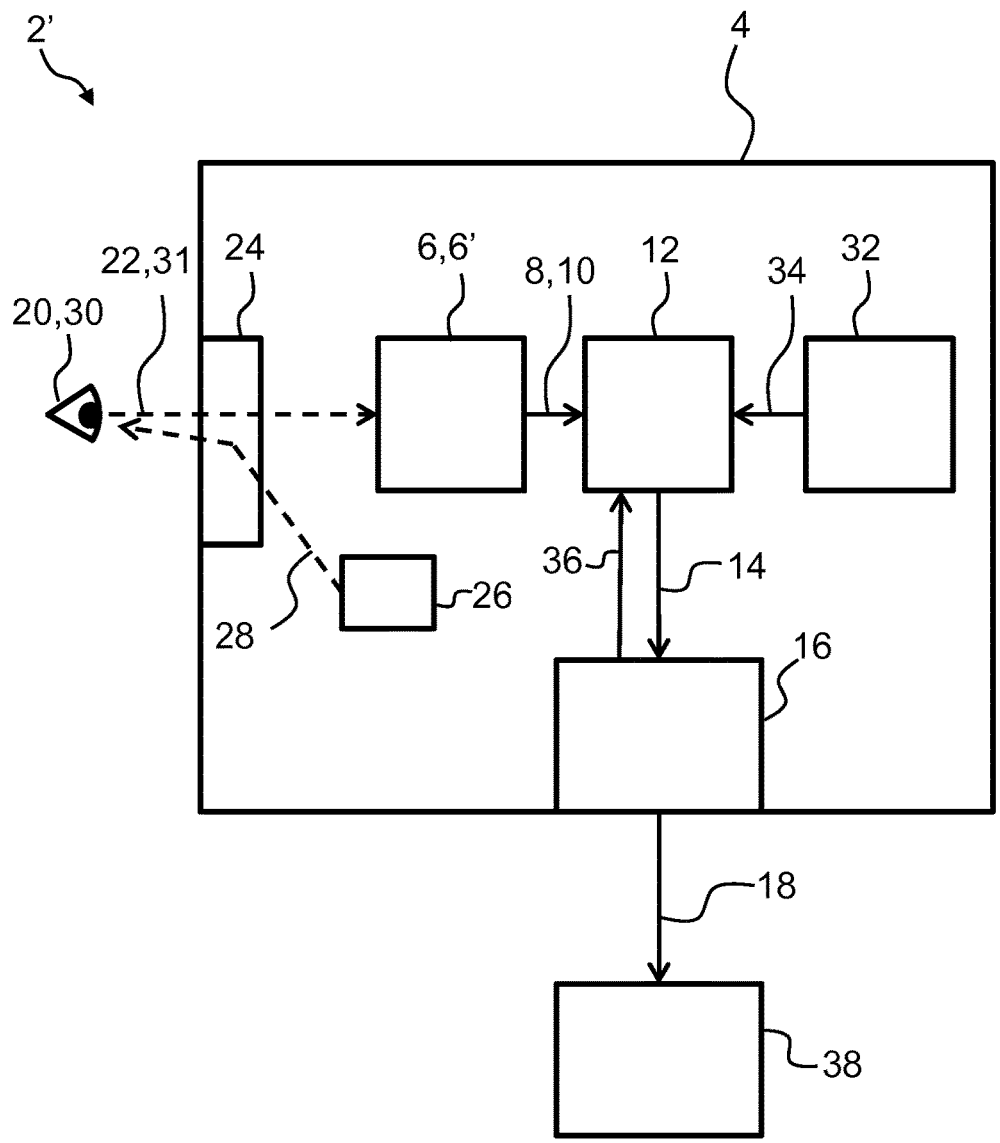
FIG. 2 schematically illustrates an exemplary head mountable device.

FIG. 2 schematically illustrates an exemplary head mountable device 2' comprising the same features as the head mountable device 2 of FIG. 1. The head mountable device 2' further comprises a number of additional features, which individually and/or in combination may be added to the head mountable device 2 of FIG. 1.

The head mountable device 2' further comprises a first light source 26. The first light source 26 is configured to emit first electromagnetic radiation 28 towards the first eye 20 and/or the second eye 30. The first electromagnetic radiation 28 may be infrared radiation (IR), laser light, and/or colored visible light, e.g. red, blue, green, and/or orange visible light.

The head mountable device 2' further comprises a first mirror 24. The first mirror 24 may be configured to mirror images 22, 31 of the first eye 20 and/or the second eye 30 towards the camera system 6, 6' and/or towards a camera of the camera system, e.g. a first camera of the camera system 6, 6' and/or a second camera of the camera system 6, 6'. Alternatively and/or additionally, the first mirror 24 may be configured to direct the first electromagnetic radiation 28, or at least a part of the first electromagnetic radiation 28, towards the first eye 20.

The head mountable device 2' further comprises a first motion sensor 32. The processing unit 12 is connected to the first motion sensor 32. The first motion sensor 32 is configured to detect movement of the head mountable device 2. The first motion sensor 32 provides a sensor output 34. The processing unit 12 is configured to process the sensor output 34 from the first motion sensor 32, and the processing unit output 14 is based on the sensor output 34.

The processing unit output 14 may be based on one or more of the sensor output 32, the first set of images 8 and the second set of images 10.

The interface 16 of the head mountable device 2' further provides a control signal 36. For example, the interface 16 may comprise an input device, which enables user control of the head mountable device. The control signal 36 is received by the processing unit 12 for controlling the head mountable device 2'.

The frame 4 comprises the camera system 6, 6', the processing unit 12, the interface 16, the first mirror 24, the first light source 26 and the first motion sensor 32. In other exemplary head mountable devices (not shown), the frame 4 may comprise one or more of the camera system 6, 6', the processing unit 12, the interface 16, the first mirror 24, the first light source 26 and the first motion sensor 32.

The head mountable device 2' may transmit, e.g. via a wireless transmitter, the device output 18, or a part of the device output 18, to an external device, such as an external display 38, e.g. a smart phone, a tablet computer, or a personal computer. The external display is external to the head mountable device 2', i.e. the frame 4 does not comprise the external display.

The processing unit output 14 may be indicative of a vestibular parameter of the user. For example, the processing unit 12 may receive the sensor output 34 and a set of images, e.g. the first set of images 8 and/or the second set of images 10. Hence, the vestibular parameter of the user may be based on the sensor output 34 and the set of images, e.g. the first set of images 8 and/or the second set of images 10. The device output 18 may consequently also be indicative of the vestibular parameter of the user.

The processing unit output 14 may be indicative of a neurologic parameter of the user. For example, the processing unit 12 may receive the sensor output 34 and a set of images, e.g. the first set of images 8 and/or the second set of images 10. Hence, the neurologic parameter of the user may be based on the sensor output 34 and the set of images, e.g. the first set of images 8 and/or the second set of images 10. The device output 18 may consequently also be indicative of the neurologic parameter of the user.

Figure 3:
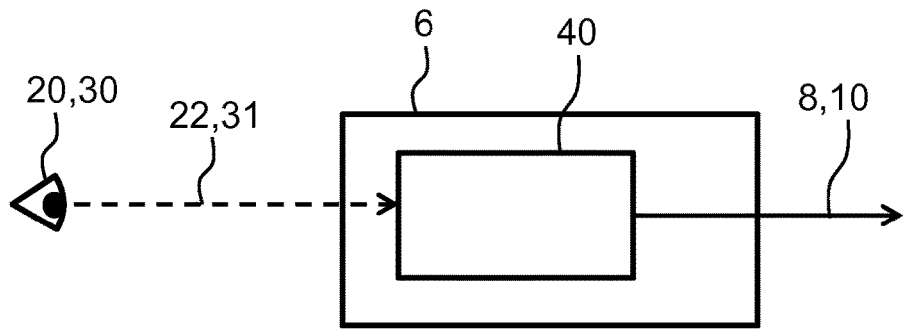
FIG. 3 schematically illustrates an exemplary camera system for a head mountable device, FIG. 4 schematically illustrates an exemplary camera system for a head mountable device, FIG. 5 schematically illustrates an exemplary interface for a head mountable device, FIG. 6 schematically illustrates an exemplary motion sensor for a head mountable device.

FIG. 3 schematically illustrates an exemplary camera system 6 for a head mountable device 2, 2'. The camera system 6 comprises a first camera 40. The first camera 40 obtains images 22 of a first eye 20 of a user and converts the images 22 of the first eye 20 to a first set of images 8 of the first eye 20 with a first frame rate and a first resolution. Alternatively or additionally, the first camera 40 detects images 31 of a second eye 30 of the user and converts the images 31 of the second eye 30 to a second set of images 10 of the second eye 30 with a second frame rate and a second resolution.

As explained in relation to FIG. 2, the head mountable device 2, 2' may comprise a first mirror 24. The first mirror 24 may be configured to mirror images 22, 31 of the first eye 20 and/or the second eye 30 towards the first camera 40, i.e. the first camera 40 may be focused on the first eye 20 and/or the second eye 30 via the first mirror. Another exemplary head mountable device (not shown) may comprise a first mirror and a second mirror. The first mirror 24 may be configured to mirror images 22 of the first eye 20 towards the first camera 40, and the second mirror may be configured to mirror images 31 of the second eye 30 towards the first camera 40.

Figure 4:
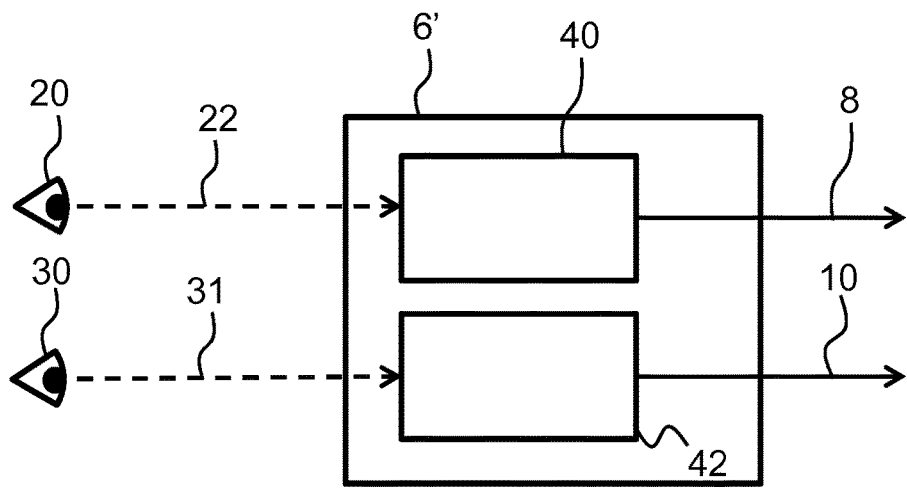

FIG. 4 schematically illustrates an exemplary camera system 6' for a head mountable device 2, 2'. The camera system 6' comprises a first camera 40 and a second camera 42. The first camera 40 detects images 22 of a first eye 20 and converts the images 22 of the first eye 20 to a first set of images 8 of the first eye 20 with a first frame rate and a first resolution. The second camera 42 detects images 31 of a second eye 30 and converts the images 31 of the second eye 30 to a second set of images 10 of the second eye 30 with a second frame rate and a second resolution.

As explained in relation to FIGS. 1-2, the head mountable device 2, 2' may comprise a first mirror 24. The first mirror 24 may be configured mirror images 22, 31 of the first eye 20 and/or the second eye 30 towards the first camera 40 and/or the second camera 42, i.e. the first camera 40 and/or the second camera 42 may be focused on the first eye 20 and/or the second eye 30, respectively, via the first mirror 24. Another exemplary head mountable device (not shown) may comprise a first mirror and a second mirror. The first mirror 24 may be configured to mirror images 22 of the first eye 20 towards the first camera 40, i.e. the first camera 40 may be focused on the first eye 20 via the first mirror, and the second mirror may be configured to mirror images 31 of the second eye 30 towards the second camera 42, i.e. the second camera 42 may be focused on the second eye 30 via the second mirror.

In relation to any of FIGS. 3 and 4, the first camera 40 and/or the second camera 42 is adapted to enable detection of eye saccades of the first eye 20 and/or second eye 30. For example, the first frame rate and/or the second frame rate may be higher than 125 fps.

The first camera 40 and/or the second camera 42 may be able to detect electromagnetic radiation such as infrared radiation (IR), laser light, and/or colored visible light, e.g. red, blue, green, and/or orange visible light. The first camera 40 and/or the second camera 42 may be able to detect the first electromagnetic radiation 28 of the first light source 26 (FIG. 2).

The first mirror 24 and/or the second mirror (not shown) may be partly transparent, such as to allow passage of electromagnetic radiation of a first range of wavelengths, e.g. visible light, and to reflect electromagnetic radiation of a second range of wavelengths e.g. infrared radiation (IR). The second range of wavelengths may include wavelengths of the electromagnetic radiation 28 of the first light source 26.

Figure 5:
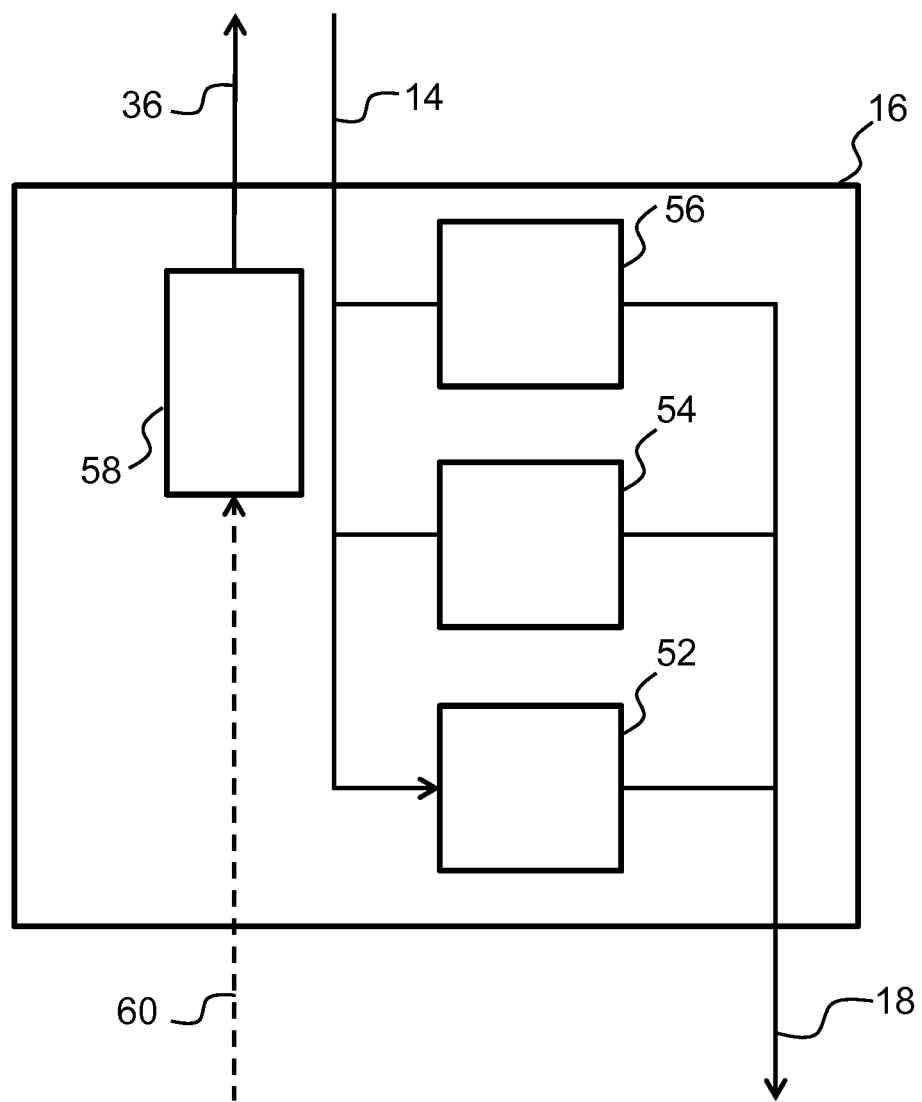

FIG. 5 schematically illustrates an exemplary interface 16 for a head mountable device 2, 2'. The exemplary interface 16 comprises a wireless transmitter unit 52, a first display 54, a speaker 56, and/or an input device 58. The interface 16 may in an alternative configuration (not shown) comprise one or more of the wireless transmitter unit 52, the first display 54, the speaker 56 and the input device 58.

The wireless transmitter unit 52 receives the processing unit output 14, or part of the processing unit output 14, and transmits the device output 18, or a part of the device output 18, wirelessly to a wireless receiver (not shown), e.g. an external device 38 as illustrated in FIG. 2. The wireless transmitter may be a Bluetooth transmitter, a WiFi transmitter, a 3G transmitter and/or a 4G transmitter. The wireless transmitter unit 52 may further be configured to transmit the device output 18, or a part of the device output 18, with a low latency to enable live preview of the device output 18 in an external display. The latency may be less than 40 ms such as less than 20 ms such as less than 10 ms.

The first display 54 receives the processing unit output 14, or part of the processing unit output 14, and visually presents the device output 18, or a part of the device output 18, to a user or an operator of the device. The first display 54 may be an organic light emitting diode (OLED), an OLED display, a light emitting diode (LED), an LED display, and/or an e-ink display.

The speaker 56 receives the processing unit output 14, or part of the processing unit output 14, and audiologically presents the device output 18, or a part of the device output 18, to a user or an operator of the device.

The input device 58 enables control of the head mountable device 2, 2'. User interaction 60 is detected by the input device 58, and the input device 58 provides a control signal 36 to the processing unit 12. The input device 58 may comprise a push button, a switch, and/or a touch display.

The device output 18 may be indicative of a positive/negative result of a test. For example, the device output 18 may comprise lighting up the first display 54 in a red colour if the test result is negative, and/or lighting up the first display 54 in a green colour if the test result is positive. For example, the device output 18 is indicative of an ophthalmologic parameter of the user, the device output 18 is indicative of a vestibular parameter of the user, and/or the device output 18 is indicative of a neurologic parameter of the user.

The device output 18 may comprise a plurality of output images based on the first set of images 8 and/or based on the second set of images 10. For example, the device output 18 may provide a live preview of the images 22, 31 of the first eye 20 and/or the second eye 30. The live preview may be transmitted wirelessly via the wireless transmitter 52 to an external display, e.g. a display of an external device 38.

Figure 6:
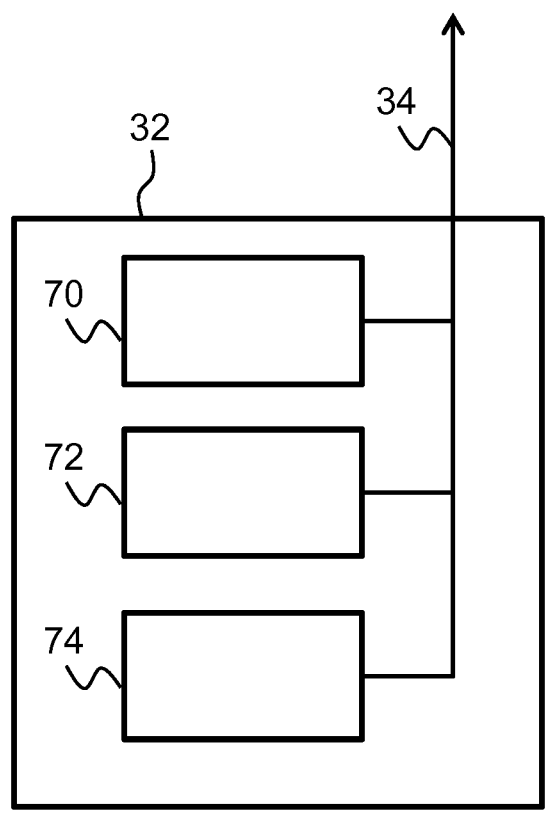

FIG. 6 schematically illustrates an exemplary motion sensor 32 for a head mountable device 2, 2'. The motion sensor 32 comprises a sensor camera 70, a sensor gyroscope 72, and/or a sensor accelerometer 74. The motion sensor 32 may in an alternative configuration (not shown) comprise one or more of the sensor camera, the sensor gyroscope, and the sensor accelerometer. The sensor camera, the sensor gyroscope, and/or the sensor accelerometer provide the sensor output 34, or one or more parts of the sensor output 34.

Figure 7:
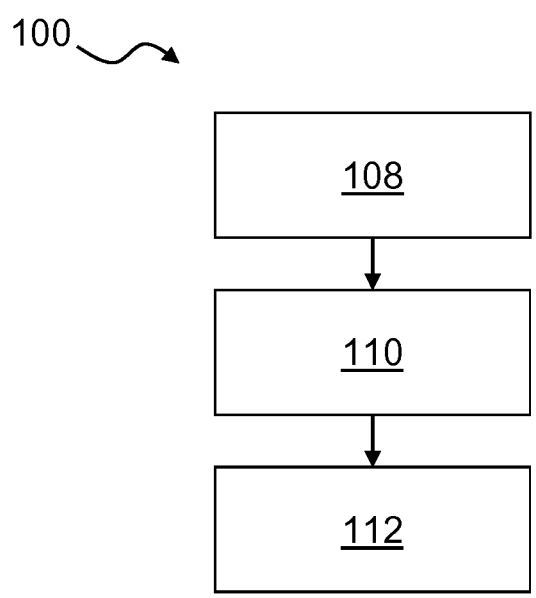
FIG. 7 shows a flow diagram of an exemplary method for measuring eye movement.

FIG. 7 shows a flow diagram of an exemplary method 100 for measuring eye movement of a user using a head mountable device comprising a frame, a camera system, a processing unit and an interface. The method 100 comprises: obtaining 108 a first set of images of a first eye of the user; processing 110 the first set of images to provide a processing unit output; and providing 112 a device output based on the processing unit output.

The method 100 may further comprise obtaining (not shown) a second set of images of a second eye of the user, wherein the second set on images is obtained with a second frame rate enabling detection of eye saccades of the second eye, e.g. a second frame rate higher than 125 fps.

Figure 8:
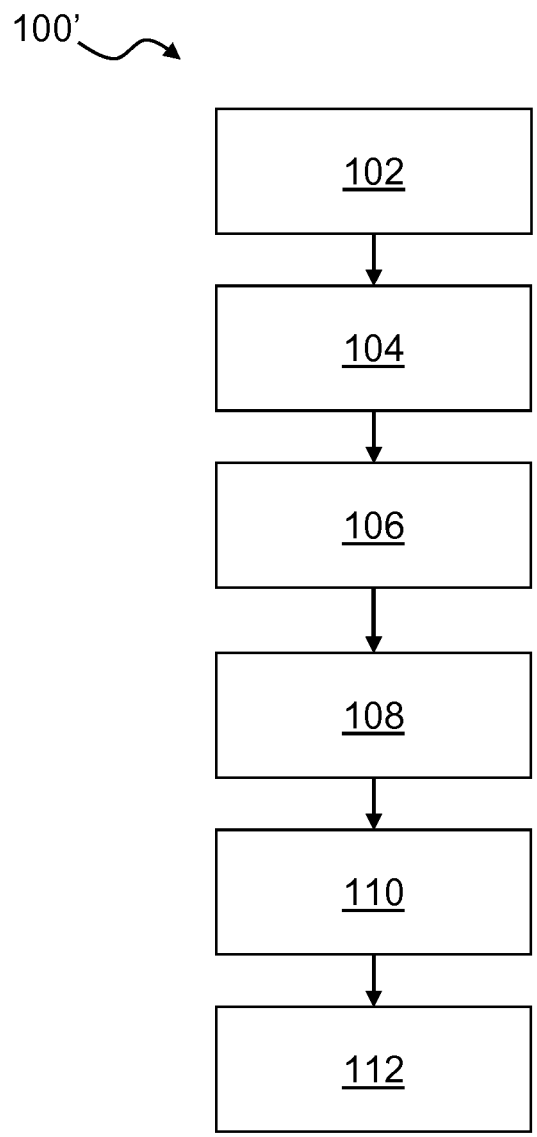
FIG. 8 shows a flow diagram of an exemplary method for measuring eye movement.

FIG. 8 shows a flow diagram of an exemplary method 100' for measuring eye movement. The method 100' comprises the same steps 108, 110, 112 as the method 100 as described in relation to FIG. 7. Additionally the method 100' comprises: mounting 102 the head mountable device to a head of the user; moving 104 the head of the user; detecting 106 movement of the head mountable device.

Mounting 102 of the head mountable device to a head of the user may be performed by an operator, and may involve fastening the head mountable device to the head of the user to avoid movement of the head mountable device relative to the head of the user. If the device is tightly fixed to the head, moving 104 the head of the user involves movement of the head mountable device, and the movement of the device directly corresponds to the movement of the head of the user. Detecting 106 of the movement of the head mountable device is therefore indicative of the moving 104 of the head of the user.

The device output provided 112 may be indicative of one or more parameters of the user, e.g. a vestibular parameter of the user, an ophthalmologic parameter of the user, and/or a neurologic parameter of the user. The device output may further be indicative of a test result, such as a vestibular test, an ophthalmologic test and/or a neurologic test. The device output may be provided 112 via an audiologic output, a visual output, and/or wireless transmission to an external device.

Embodiments and aspects are disclosed in the following items:

Item 1. A head mountable device for measuring eye movement, the head mountable device comprising:
 a frame;
 a camera system comprising a first camera, wherein the camera system is configured to obtain a first set of images of a first eye of a user with a first frame rate and a first resolution;
 a processing unit configured to process the obtained first set of images and providing a processing unit output based on the first set of images;
 an interface connected to the processing unit, for providing a device output based on the processing unit output; wherein the first frame rate is selected such as to enable the processing unit to detect eye saccades of the first eye.

Item 2. Head mountable device according to item 1, wherein the first frame rate is higher than 125 frames per second.

Item 3. Head mountable device according to any of items 1 or 2, wherein the head mountable device comprises a first mirror for mirroring images of the first eye towards the first camera.

Item 4. Head mountable device according to any of the preceding items, wherein the head mountable device comprises a first light source for emitting first electromagnetic radiation towards the first eye.

Item 5. Head mountable device according to item 4, wherein the first mirror is configured to direct at least a part of the first electromagnetic radiation towards the first eye.

Item 6. Head mountable device according to any of the preceding items, wherein the camera system is configured to obtain a second set of images of a second eye of the user with a second frame rate, wherein the second frame rate is selected such as to enable the processing unit to detect eye saccades of the second eye.

Item 7. Head mountable device according to item 6, wherein the second frame rate is higher than 125 frames per second.

Item 8. Head mountable device according to any of items 6 or 7, wherein the camera system comprises a second camera configured to obtain the second set of images.

Item 9. Head mountable device according to any of the preceding items, wherein the processing unit output is indicative of an ophthalmologic parameter of the user.

Item 10. Head mountable device according to any of the preceding items, wherein the frame comprises the camera system, the processing unit, and the interface.

Item 11. Head mountable device according to any of the preceding items, wherein the processing unit is connected to a first motion sensor configured to detect movement of the head mountable device, and wherein the processing unit is configured to process a sensor output from the first motion sensor and wherein the processing unit output is based on the sensor output.

Item 12. Head mountable device according to item 11, wherein the first motion sensor comprises a camera and/or a gyroscope and/or an accelerometer.

Item 13. Head mountable device according to any of items 11 or 12, wherein the processing unit output is indicative of a vestibular parameter of the user.

Item 14. Head mountable device according to item 13, wherein the processing unit receives the sensor output and the first set of images, and wherein the vestibular parameter of the user is based on the sensor output and the first set of images.

Item 15. Head mountable device according to any of items 11-14, wherein the processing unit output is indicative of a neurologic parameter of the user.

Item 16. Head mountable device according to item 15, wherein the processing unit receives the sensor output and the first set of images, and wherein the neurologic parameter of the user is based on the sensor output and the first set of images.

Item 17. Head mountable device according to any of items 11-16, wherein the frame comprises the first motion sensor.

Item 18. Head mountable device according to any of the preceding items, wherein the interface comprises a wireless transmitter unit.

Item 19. Head mountable device according to item 18, wherein the wireless transmitter unit is configured to transmit the device output to an external display, wherein the external display is external to the head mountable device.

Item 20. Head mountable device according to item 19, wherein the wireless transmitter unit is configured to transmit the device output to the external display with a latency of less than 10 ms from the obtaining of the first set of images.

Item 21. Head mountable device according to any of the preceding items, wherein the processing unit output comprises a first secondary set of images with a first secondary frame rate and a first secondary resolution.

Item 22. Head mountable device according to item 21, wherein the first secondary frame rate is smaller than the first frame rate and/or the first secondary resolution is smaller than the first resolution.

Item 23. Head mountable device according to any of the preceding claims, wherein the processing unit is configured to compress an initial processing unit output based on the first set of images, wherein the size of the processing unit output is below 5% of the size of the initial processing unit output.

Item 24. Head mountable device according to any of the preceding items, wherein the interface comprises a first display.

Item 25. Head mountable device according to any of the preceding items, wherein the interface comprises a speaker.

Item 26. Head mountable device according to any of the preceding items, wherein the interface comprises an input device for enabling control of the head mountable device.

Item 27. Head mountable device according to any of the preceding items, wherein the processing unit output is indicative of a test result.

Item 28. Head mountable device according to any of the preceding items, wherein the processing unit output comprises a plurality of output images based on the first set of images.

Item 29. Method for measuring eye movement of a user using a head mountable device comprising a frame, a camera system, a processing unit and an interface connected to the processing unit, the method comprising:
  obtaining a first set of images of a first eye of the user by the camera system, with a first frame rate and a first resolution, wherein the first frame rate is selected such as to enable the processing unit to detect eye saccades of the first eye;
  processing the obtained first set of images by the processing unit to provide a processing unit output based on the first set of images;
  providing a device output by the interface based on the processing unit output.

Item 30. Method according to item 29, wherein the first frame rate is higher than 125 frames per second.

Item 31. Method according to any of items 29-30, wherein the method further comprises mounting the head mountable device to a head of the user.

Item 32. Method according to any of items 29-31, wherein the head mountable device comprises a first motion sensor, and wherein the method further comprises detecting movement of the head mountable device by the first motion sensor.

Item 33. Method according to item 32, wherein the method further comprises moving the head of the user.

Item 34. Method according to any of items 29-33, wherein the device output is indicative of a vestibular parameter of the user.

Item 35. Method according to any of items 29-34, wherein the device output is indicative of an ophthalmologic parameter of the user.

Item 36. Method according to any of items 29-35, wherein the device output is indicative of a neurologic parameter of the user.

Item 37. Method according to any of items 29-36, wherein the device output comprises an audiologic output.

Item 38. Method according to any of items 29-37, wherein the device output comprises a visual output.

Item 39. Method according to any of items 29-38, wherein providing the device output comprises transmitting the device output wirelessly to an external display.

Item 40. Method according to any of items 29-39, wherein the device output is indicative of a test result.

Item 41. A head mountable device for measuring eye movement, comprising:
  a camera system comprising a first camera, wherein the camera system is configured to obtain a first set of images of a first eye of a user with a first frame rate and a first resolution;
  a processing unit configured to process the obtained first set of images and provide a processing unit output based on the first set of images; and
  an interface connected to the processing unit, for providing a device output based on the processing unit output;
  wherein the first frame rate is sufficient to allow the processing unit to detect eye saccades of the first eye.

Item 42. The head mountable device according to item 41, wherein the first frame rate is higher than 125 frames per second.

Item 43. The head mountable device according to item 41, further comprising a first mirror for mirroring images of the first eye towards the first camera.

Item 44. The head mountable device according to item 43, further comprising a first light source for emitting first electromagnetic radiation towards the first eye.

Item 45. The head mountable device according to item 44, wherein the first mirror is configured to direct at least a part of the first electromagnetic radiation towards the first eye.

Item 46. The head mountable device according to item 41, wherein the camera system is configured to obtain a second set of images of a second eye of the user with a second frame rate, wherein the second frame rate is sufficient to allow the processing unit to detect eye saccades of the second eye.

Item 47. The head mountable device according to item 46, wherein the second frame rate is higher than 125 frames per second.

Item 48. The head mountable device according to item 46, wherein the camera system comprises a second camera configured to obtain the second set of images.

Item 49. The head mountable device according to item 41, wherein the processing unit output is indicative of an ophthalmologic parameter of the user.

Item 50. The head mountable device according to item 41, further comprising a frame, wherein the camera system, the processing unit, and the interface are mounted to the frame.

Item 51. The head mountable device according to item 41, further comprising a first motion sensor configured to detect a movement of the head mountable device;
  wherein the processing unit is connected to the first motion sensor;
  wherein the processing unit is configured to process a sensor output from the first motion sensor; and
  wherein the processing unit output is also based on the sensor output.

Item 52. The head mountable device according to item 51, wherein the first motion sensor comprises a camera, a gyroscope, an accelerometer, or any combination of the foregoing; and wherein the camera is the first camera or another camera.

Item 53. The head mountable device according to item 51, wherein the processing unit output is indicative of a vestibular parameter of the user.

Item 54. The head mountable device according to item 53, wherein the processing unit is configured to receive the sensor output and the first set of images, and wherein the vestibular parameter of the user is based on the sensor output and the first set of images.

Item 55. The head mountable device according to item 51, wherein the processing unit output is indicative of a neurologic parameter of the user.

Item 56. The head mountable device according to item 55, wherein the processing unit is configured to receive the sensor output and the first set of images, and wherein the neurologic parameter of the user is based on the sensor output and the first set of images.

Item 57. The head mountable device according to item 41, further comprising a frame, wherein the first motion sensor is mounted to the frame.

Item 58. The head mountable device according to item 41, wherein the interface comprises a wireless transmitter unit.

Item 59. The head mountable device according to item 58, wherein the wireless transmitter unit is configured to transmit the device output to an external display, and wherein the external display is external to the head mountable device.

Item 60. The head mountable device according to item 59, wherein the wireless transmitter unit is configured to transmit the device output to the external display with a latency of less than 10 ms from a time when the first set of images is obtained by the camera system.

Item 61. The head mountable device according to item 41, wherein the processing unit output comprises a first secondary set of images with a first secondary frame rate and a first secondary resolution.

Item 62. The head mountable device according to item 61, wherein the first secondary frame rate is smaller than the first frame rate, and/or the first secondary resolution is smaller than the first resolution.

Item 63. The head mountable device according to item 41, wherein the processing unit is configured to compress an initial processing unit output based on the first set of images, wherein a size of the processing unit output is below 5% of a size of the initial processing unit output.

Item 64. The head mountable device according to item 41, wherein the interface comprises a first display.

Item 65. The head mountable device according to item 41, wherein the interface comprises a speaker.

Item 66. The head mountable device according to item 41, wherein the interface comprises an input device for allowing control of the head mountable device.

Item 67. The head mountable device according to item 41, wherein the processing unit output is indicative of a test result.

Item 68. The head mountable device according to item 41, wherein the processing unit output comprises a plurality of output images based on the first set of images.

Item 69. A method for measuring eye movement of a user using a head mountable device comprising a camera system, a processing unit, and an interface connected to the processing unit, the method comprising:

obtaining a first set of images of a first eye of the user by the camera system, the first set of images having a first frame rate and a first resolution, wherein the first frame rate is sufficient to allow the processing unit to detect eye saccades of the first eye;

processing the obtained first set of images by the processing unit to provide a processing unit output based on the first set of images; and providing a device output by the interface based on the processing unit output.

Item 70. The method according to item 69, wherein the first frame rate is higher than 125 frames per second.

Item 71. The method according to item 69, further comprising mounting the head mountable device to a head of the user.

Item 72. The method according to item 69, wherein the head mountable device comprises a first motion sensor, and wherein the method further comprises detecting a movement of the head mountable device by the first motion sensor.

Item 73. The method according to item 69, wherein the device output is indicative of a vestibular parameter of the user.

Item 74. The method according to item 69, wherein the device output is indicative of an ophthalmologic parameter of the user.

Item 75. The method according to item 69, wherein the device output is indicative of a neurologic parameter of the user.

Item 76. The method according to item 69, wherein the device output comprises an audiologic output.

Item 77. The method according to item 69, wherein the device output comprises a visual output.

Item 78. The method according to item 69, wherein the act of providing the device output comprises transmitting the device output wirelessly to an external display.

Item 79. The method according to item 69, wherein the device output is indicative of a test result.

Although particular embodiments have been shown and described, it will be understood that it is not intended to limit the claimed inventions. The specification and drawings are, accordingly, to be regarded in an illustrative rather than restrictive sense. The claimed inventions are intended to cover alternatives, modifications, and equivalents.

LIST OF REFERENCES 2, 2' head mountable device
4 frame
6, 6' camera system
8 first set of images
10 second set of images
12 processing unit
14 processing unit output
16 interface
18 device output
20 first eye
22 image of first eye
24 first mirror
26 first light source
28 first electromagnetic radiation
30 second eye
31 image of second eye
32 first motion sensor
34 sensor output
36 control signal
38 external display
40 first camera
42 second camera
52 wireless transmitter unit 54 first display
56 speaker
58 input device
60 user interaction
70 sensor camera
72 sensor gyroscope
74 sensor accelerometer
100, 100' method for measuring eye movement
102 mounting
104 moving
106 detecting movement
108 obtaining set of images
110 processing set of images
112 providing device output

The invention claimed is:

1. A head mountable device for measuring eye movement, comprising:
　a camera system comprising a first camera, wherein the camera system is configured to obtain a first set of images of a first eye of a user with a first frame rate and a first resolution, wherein the first camera detects images of a second eye of the user and converts the images of the second eye to a second set of images;
　a first light source configured to emit a first electromagnetic radiation towards the first eye of the user;
　a first mirror configured to direct at least a part of the first electromagnetic radiation towards the first eye and to reflect images of the first eye towards the first camera of the camera system by focusing the first camera on the first eye;
　a processing unit in the head mountable device, the processing unit configured to process the obtained first set of images and provide a processing unit output based on the first set of images, and the processing unit compresses an amount of data in the processing unit output;
　an interface connected to the processing unit, for providing a device output based on the processing unit output, the interface further provides a control signal to the processing unit; and
　a motion sensor configured to detect a movement of the head mountable device;
wherein the first frame rate is sufficient to allow the processing unit to detect eye saccades of the first eye.

2. The head mountable device according to claim 1, wherein the camera system is configured to obtain the second set of images of the second eye of the user with a second frame rate, wherein the second frame rate is sufficient to allow the processing unit to detect eye saccades of the second eye.

3. The head mountable device according to claim 2, wherein the camera system comprises a second camera configured to obtain the second set of images.

4. The head mountable device according to claim 1,
　wherein the processing unit is connected to the first motion sensor;
　wherein the processing unit is configured to process a sensor output from the first motion sensor; and
　wherein the processing unit output is also based on the sensor output.

5. A head mountable device for measuring eye movement, comprising:
　a camera system comprising a first camera, wherein the camera system is configured to obtain a first set of images of a first eye of a user with a first frame rate and a first resolution, wherein the first camera detects images of a second eye of the user and converts the images of the second eye to a second set of images;
　a first light source configured to emit a first electromagnetic radiation towards the first eye of the user;
　a first mirror configured to direct at least a part of the first electromagnetic radiation towards the first eye and to reflect images of the first eye towards the first camera of the camera system by focusing the first camera on the first eye;
　a processing unit in the head mountable device, the processing unit configured to process the obtained first set of images and provide a processing unit output based on the first set of images; and
　an interface connected to the processing unit, for providing a device output based on the processing unit output, the interface further provides a control signal to the processing unit;
　wherein the first frame rate is sufficient to allow the processing unit to detect eye saccades of the first eye;
　wherein the processing unit compresses an amount of data in the processing unit output, the compression enables the interface to transmit the device output without a substantial delay;
　wherein the interface comprises a wireless transmitter unit.

6. The head mountable device according to claim 5, wherein the wireless transmitter unit is configured to transmit the device output to an external display, and wherein the external display is external to the head mountable device.

7. The head mountable device according to claim 1, wherein the interface comprises a first display.

8. A method for measuring eye movement of a user using a head mountable device comprising a camera system, a first light source, a first mirror, a processing unit, and an interface connected to the processing unit, the method comprising:
　obtaining a first set of images of a first eye of the user by a first camera of the camera system of the head mountable device, the first set of images having a first frame rate and a first resolution, wherein the first frame rate is sufficient to allow the processing unit to detect eye saccades of the first eye;
　processing the obtained first set of images by the processing unit of the head mountable device to provide a processing unit output based on the first set of images;
　compressing an amount of data in the processing unit output by the processing unit; and
　providing a device output by the interface based on the processing unit output;
　wherein the head mountable device comprises a first motion sensor, and wherein the method further comprises detecting a movement of the head mountable device by the first motion sensor.

9. The method according to claim 8, further comprising mounting the head mountable device to a head of the user.

10. The method according to claim 8, wherein the device output comprises a visual output.

11. The method according to claim 8, wherein the act of providing the device output comprises transmitting the device output wirelessly to an external display.

12. The method according to claim 8, wherein the camera system comprises a second camera configured to obtain a second set of images of a second eye of the user with a second frame rate.

13. The method according to claim 8, further comprising providing mirroring images of the second eye of the user by a second mirror towards the first camera.

14. The head mountable device according to claim 5, wherein the first mirror provides mirroring images of the first eye towards a second camera.

15. The head mountable device according to claim 2, wherein the first mirror is partly transparent to allow passage of electromagnetic radiation of a first range of wavelengths.

* * * * *